US008778684B2

(12) United States Patent
Brown et al.

(10) Patent No.: US 8,778,684 B2
(45) **Date of Patent: *Jul. 15, 2014**

(54) HERPES SIMPLEX VIRUS COMPLEX

(75) Inventors: Susanne Moira Brown, Glasgow (GB); Joe Conner, Glasgow (GB)

(73) Assignee: Virttu Biologics Limited, Glasgow (GB)

( * ) Notice: Subject to any disclaimer, the term of this patent is extended or adjusted under 35 U.S.C. 154(b) by 659 days.

This patent is subject to a terminal disclaimer.

(21) Appl. No.: 13/086,215

(22) Filed: Apr. 13, 2011

(65) Prior Publication Data

US 2011/0244576 A1 Oct. 6, 2011

Related U.S. Application Data

(63) Continuation of application No. 10/504,460, filed as application No. PCT/GB03/00603 on Feb. 12, 2003, now Pat. No. 7,943,144.

(30) Foreign Application Priority Data

Feb. 12, 2002 (GB) .................................. 0203285.2

(51) Int. Cl.
*C12N 15/64* (2006.01)
*C12N 15/869* (2006.01)

(52) U.S. Cl.
USPC ......................... 435/475; 435/235.1; 435/239

(58) Field of Classification Search
None
See application file for complete search history.

(56) References Cited

U.S. PATENT DOCUMENTS

| | | | | |
|---|---|---|---|---|
| 6,139,834 | A | 10/2000 | Martuza et al. | |
| 6,235,467 | B1 | 5/2001 | Brown et al. | |
| 6,673,602 | B1 | 1/2004 | Spear et al. | |
| 7,943,144 | B2 * | 5/2011 | Brown et al. | 424/199.1 |

FOREIGN PATENT DOCUMENTS

| | | | |
|---|---|---|---|
| GB | 2374873 | | 10/2002 |
| JP | 6-507066 | | 8/1994 |
| WO | WO 92/13943 | A1 | 8/1992 |
| WO | 96/03997 | | 2/1996 |
| WO | 98/39467 | | 9/1998 |
| WO | WO 98/42195 | A1 | 10/1998 |
| WO | WO 99/06583 | A1 | 2/1999 |
| WO | 00/08191 | | 2/2000 |
| WO | WO 01/16331 | A1 | 3/2001 |
| WO | WO 2004/033639 | A2 | 4/2004 |
| WO | WO 2009/013448 | A2 | 1/2009 |

OTHER PUBLICATIONS

Ager, et al., "Retroviral Display of Antibody Fragments; Interdomain Spacing Strongly Influences Vector Infectivity," (Nov. 10, 1996) Human Gene Therapy, 7:2157-2164.

Arakawa, et al., "Targeting of T Cells to CEA-expressing Tumor Cells by Chimeric Immune Receptors with a Highly Specific Single-chain Anti-CEA Activity," (2002) Anticancer Research, 22:4285-4290.

Argnani et al., "Specific targeted binding of herpes simplex virus type 1 to hepatocytes via the human hepatitis B virus preS1 peptide," Gene Therapy, 2004, vol. 11:1087-1098, Nature Publishing Group.

Benedict, et al., "Targeting Retroviral Vectors to CD34-Expressing Cells: Binding to CD 34 Does Not Catalyze Virus-Cell Fusion," (Mar. 1, 1999) Human Gene Therapy, 10:545-557.

Bucheit, et al., "An Oncolytic Measles Virus Engineered to Enter Cells Through the CD20 Antigen," (Jan. 2003) Molecular Therapy, 7(1):62-72.

Chung, et al. "B-*myb* Promoter Retargeting of Herpes Simplex Virus γ34.5 Gene-Mediated Virulence toward Tumor and Cycling Cells" Journal of Virology (1999) 73(9):7556-7564.

Conner et al., "Herpes Simplex Virus Type 1 Strain HSV1716 Grown in Baby Hamster Kidney Cells Has Altered Tropism for Nonpermissive Chinese Hamster Ovary Cells Compared to HSV1716 Grown in Vero Cells," (Aug. 2005) Journal of Virology, 79(15):9970-9981.

Conner, et al. "A strategy for systemic delivery of the oncolytic herpes virus HSV1716: redirected tropism by antibody-binding sites incorporated on the virion surface as a glycoprotein D fusion protein," (2008) Gene Therapy, pp. 1-14.

Dolter et al., "Incorporation of CD4 into Virions by a Recombinant Herpes Simplex Virus," (Jan. 1993) Journal of Virology, 67(1):189-195.

Douglas, et al., "Targeted gene delivery by tropism-modified adenoviral vectors," (Nov. 1996) Nature Biotechnology 14:1574-1578.

Engelstadter, et al., "Targeting Human T Cells by Retroviral Vectors Displaying Antibody Domains Selected from a Phage Display Library," (Jan. 20, 2000) Human Gene Therapy, 11:293-303.

Fields Virology, Chapter 55: *Retroviridae: The Retroviruses and Their Replication*, Goff, Stephen P., pp. 2000-2069, Fifth Edition, Lippincott Williams & Wilkins 2007 ISBN-13 978-0-7417-6060-7.

Fields Virology, Chapter 63: *Adenoviridae: The Viruses and Their Replication*, Berk, Arnold J., pp. 2355-2394, Fifth Edition, Lippincott Williams & Wilkins 2007 ISBN-13 978-0-7417-6060-7.

Fields Virology, Chapter 67: *Herpes Simplex Viruses*, Roizman, Bernard; Knipe, David M.; and Whitley, Richard J., pp. 2502-2601, Fifth Edition, Lippincott Williams & Wilkins 2007 ISBN-13 978-0-7417-6060-7.

Galmiche, et al., "Expression of a functional single chain antibody on the surface of extracellular enveloped *Vaccinia virus* as a step towards selective tumour cell targeting," (1997) J. of General Virology, 78:3019-3027.

Grandi, et al., "Targeting HSV-1 virions for specific binding to epidermal growth factor receptor-vIII- bearing tumor cells," (2010) Cancer Gene Therapy, pp. 1-9.

(Continued)

*Primary Examiner* — Mary E Mosher
(74) *Attorney, Agent, or Firm* — Swanson & Bratschun L.L.C.

(57) ABSTRACT

There is provided an HSV complex which comprises an avirulent HSV and a targeting agent which allows the HSV particle to infect and lyse a specific targeted cell. The inventors have found a way in which avirulent HSV can be targeted to disease cells, e.g. cancer cells, by incorporating an antibody binding domain into one or more viral glycoproteins.

13 Claims, 5 Drawing Sheets

(56) References Cited

OTHER PUBLICATIONS

Figure 1:
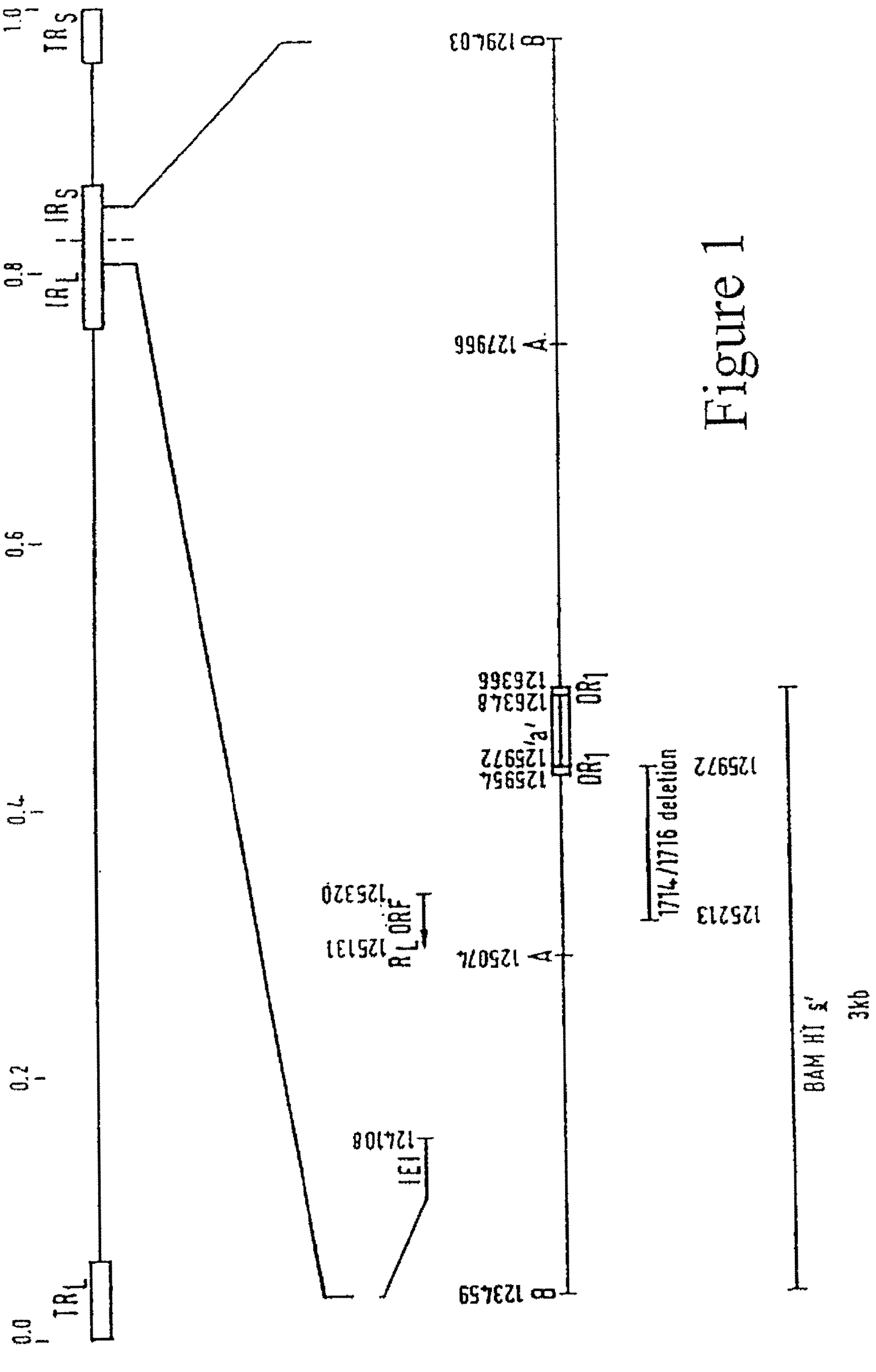

Grandi, Paola et al., "HSV-1 Virions Engineered for Specific Binding to Cell Surface Receptors," Molecular Therapy, vol. 9, No. 3, Mar. 2004, pp. 419-427, The American Society of Gene Therapy.
Hammond et al., "Single-Chain Antibody Displayed on a Recombinant Measles Virus Confers Entry through the Tumor-Associated Carcinoembryonic Antigen," (Mar. 2001) Journal of Virology, pp. 2087-2096.
Khare, et at. "Specifically Targeted Killing of Carcinoembryonic Antigen (CEA)-expressing Cells by a Retroviral Vector Displaying Single-Chain Variable Fragmented Antibody to CEA and Carrying the Gene for Inducible Nitric Oxide Synthase," (Jan. 1, 2001) Cancer Research, 61:370-375.
Kirn et al, "Replication-selective virotherapy for cancer: Biological principles, risk management and future directions," (Jul. 2001) Nature Medicine. 7(7):782-787.
Konishi, et al., "Targeting Strategy for Gene Delivery to Carcinoembryonic Antigen-Producing Cancer Cells by Retrovirus Displaying a Single-Chain Variable Fragment Antibody," (Jan. 20, 1998) Human Gene Therapy, 9:235-248.
Kuroki, et al., "Specific Targeting Strategies of Cancer Gene Therapy Using a Single chain Variable Fragment (scFv) with a High Affinity for CEA," (2000) Anticancer Research, 20:4067-4072.
Laquerre, et al., "Recombinant Herpes Simplex Virus Type 1 Engineered for Targeted Binding to Erythropoietin Receptor-Bearing Cells," (Dec. 1998) J. of Virology, 72(12):9683-9697.
Lilley, et al., "Multiple Immediate-Early Gene-Deficient Herpes Simplex Virus Vectors Allowing Efficient Gene Delivery to Neurons in Culture and Widespread Gene Delivery to the Central Nervous System in Vivo," (May 2001) J. of Virology, 75(9):4343-4356.
Lorimer, et al., "Targeting retrovirus to cancer cells expressing a mutant EGF receptor by insertion of a single chain antibody variable domain in the envelope glycoprotein receptor binding lobe," (2000), Journal of Immunological Methods, 237:147-157.
Mackie et al., "Intralesional injection of herpes simplex virus 1716 in metastatic melanoma" The Lancet (Feb. 2001) 357:525-526.
MaClean, et al., "Herpes simplex virus type 1 deletion variants 1714 and 1716 pinpoint neurovirulence-related sequences in Glasgow strain 17$^+$between immediate early gene 1 and the 'a' sequence," (1991), Journal of General Virology 72:631-639.
Marin, et al., "Targeted Infection of Human Cells via Major Histocompatibility Complex Class I Molecules by Moloney Murine Leukemia Virus-Derived Viruses Displaying Single-Chain Antibody Fragment-Envelope Fusion Proteins," (May 1996) J. of Virology, 70(5):2957-2962.
Martin, et al., "Retrovirus Targeting by Tropism Restriction to Melanoma Cells," (Aug. 1999) J. of Virology, 73(8):6923-6929.
Martin, et al., "Retroviral Vector Targeting to Melanoma Cells by Single-Chain Antibody Incorporation in Envelope," (Mar. 20, 1998) Human Gene Therapy, 9:737-746.
McKie, et al., "Histopathological responses in the CNS following inoculation with a non-nonneurovirulent mutant (1716) of herpes simplex virus type 1 (HSV 1): relevance for gene and cancer therapy," (1998) Neuropathol of [J] and Applied Neurobiolof [J], 24:367-372.
McKie, et al., "Selective astrocytic transgene expression in vitro and in vivo from the GFAP promoter in a HSV RLI null mutant vector-potential glioblastoma targeting," (1998) Gene Therapy, 5:440-450.
McKie, et al., "Selective in vitro replication ofherpes simplex virus type 1 (HSV-I) ICP34.5 null mutants in primary human CNS tumours-evaluation of a potentially effective clinical therapy," British J of Cancer, (1996) 74:745-752.
Menotti, "Inhibition of human tumor growth in mice by an oncolytic herpes simples virus designed to target solely HER-2-positive cells" (2009) PNAS, 106(22): 9039-9044.
Menotti, et al., "A herpes simplex virus recombinant that exhibits a single-chain antibody to HER2/neu enters cells through the mammary tumor receptor, independently of the gD receptors" (2006) Journal of Virology, 80(11):5531-5539.
Menotti, et al., "Construction of a Fully Retargeted Herpes Simplex Virus 1 Recombinant Capable of Entering Cells Solely via Human Epidermal Growth Factor Receptor 2," (Oct. 2008) Journal of Virology, 82(20):10154-10161.
Moss, "Poxviridae: The Viruses and Their Replication" (2007) Fields Virology, 5th Ed.:2905-2945.
Nakano et al., "Herpes Simplex Virus Targeting to the EGF Receptor by a gD-Specific Soluble Bridging Molecule" (Apr. 2005) Molecular Therapy, 11(4):617-626.
Ojala, et al., "Specific Binding of Baculoviruses Displaying gp64 Fusion Proteins to Mammalian Cells," Biochemical and Biophysical Research Communications, (2001), 284:777-784.
Peng, et al., "Oncolytic measles viruses displaying a single-chain antibody against CD38, a mycloma cell marker," (Apr. 1, 2003) Blood, 101(7):2557-2562.
Post et al, "Replicative Oncolytic Herpes Simplex Viruses in Combination Cancer Therapies," (2004) Current Gene Therapy, 4: 41-51.
Randazzo et al, "Teatment of Experimental Subcutaneous Human Melanoma with a Replication-Restricted Herpes Simplex Virus Mutant," (1997) The Journal of Investigative Dermatology 108:933-937.
Roizman et al., "Herpes Simplex Viruses" (2007) Fields Virology, 5$^{th}$ Ed.:2501-2505, 2515-2521, 2530-2534.
Schnierle, et al., "Expression of chimeric envelope proteins in helper cell lines and integration into Moloney murine leukemia virus particles," (1996) Gene Therapy, 3:334-342.
Somia et al., "Generation of targeted retrovial vectors by using single-chain bariable gragment: An approach to in vivo gene delivery," (1995) Proc. Natl. Acad. Sci., 92:7570-7574.
Spear, et al., "HSV-I amplicon peptide display vector," (2002) J Virological Methods, 107:71-79.
Taha, et al., "A Variant of Herpes Simplex Virus Type 2 Strain HG52 with a 1'5 kb Deletion in $R_L$ between 0 and 0'02 and 0'81 to 0'83 Map Units is Non-neurovirulent for Mice," (1989) J General Virology, 70:705-716.
Tanaka, et al., "Targeted killing of carcinoembryonic antigen (CEA)-producing cholangiocarcinoma cells by polyamidoamine dendrimer-mediated transfer of an Epstein-Barr virus (EBV)-based plasmid vector carrying the CEA promoter," (2000) Cancer Gene Therapy, 7(9):1241-1249.
Tang et al., "Tumor cell-specific gene transfer with retroviral vectors displaying single-chain antibody," (2002) Chinese Medical Journal, 115(7):1064-1069.
Toda, et al., "Herpes Simplex Virus as an in Situ Cancer Vaccine for the Induction of Specific Anti-Tumor Immunity," (Feb. 10, 1999) Human Gene Therapy, 10:385-393.
Tolba et al, "Development of herpes simplex virus-1 amplicon-based immunotherapy for chronic lymphocytic leukemia," (Jul. 2001) Gene Therapy. Blood. 15 vol. 98, No. 2.
Watkins, et al., "The 'adenobody' approach to viral targeting: specific and enhanced adenoviral gene delivery," (1997) Gene Therapy 4:1004-1012.
Weng et al, "Expression of complement inhibitors CD46, CD55, and CD59 on tumor cells does not predict clinical outcome after rituximab treatment in follicular non-Hodgkin lymphoma" Blood (Sep. 2001) 98(5):1352-1357.
Wickham, "Ligand-directed targeting of genes to the site of disease," (Jan. 2003) Nature Medicine, 9(1):135-139.
Zhou et al., "Engineered herpes simplex virus 1 is dependent on IL13Ralpha 2 receptor for cell entry and independent of glycoprotein D receptor interaction" (Nov. 2002) PNAS, 99(23):15124-15129.
U.S. Appl. No. 10/504,460, Office Action dated Sep. 19, 2008, 11 pages.
U.S. Appl. No. 10/504,460, Final Rejection dated Mar. 20, 2009, 14 pages.
U.S. Appl. No. 10/504,460, Office Action dated Sep. 25, 2009, 16 pages.
U.S. Appl. No. 10/504,460, Office Action dated Jun. 8, 2010, 33 pages.
U.S. Appl. No. 10/504,460, Notice of Allowance dated Feb. 9, 2011, 17 pages.

* cited by examiner a) <u>GAATTC</u>ATGGGATGGAGCTGTATCATCCTCTTCTTGGTAGCAACAGCTACAGGTGTCCACTCCGC<u>GGCCCAGCCGGCC</u>GATGTGCAACTGGTGGAGTCT b)

HERPES SIMPLEX VIRUS COMPLEX

RELATED APPLICATIONS

This application is a continuation of U.S. application Ser. No. 10/504,460, filed on Jun. 29, 2005, which is a 35 U.S.C. §371 national phase application of PCT/GB03/00603 (WO 2003/068809) filed on Feb. 12, 2003 entitled "An Herpes Simplex Virus Complex," which application claims the benefit of Great Britain Application Serial No. 0203285.2 filed Feb. 12, 2002, each of which are incorporated herein by reference in their entirety.

FIELD OF THE INVENTION

The present invention relates to Herpes Simplex Virus (HSV) complex, including its production and its use. Particularly, but not exclusively, the invention relates to an HSV type I incorporating an antibody binding domain for targeting cells especially cancer cells.

Incorporated by reference herein in its entirety is the Sequence Listing entitled "Sequence Listing2.txt," created Jan. 11, 2011, size of 1 kilobyte.

BACKGROUND OF THE INVENTION

HSV is an enveloped, icosahedral, double-stranded DNA virus that infects mammals, including humans. Wild-type HSV infects and replicates in both terminally differentiated cells and dividing cells. Wild type HSV is neurovirulent, entering the peripheral nervous system where active viral replication is suppressed and the virus remains latent in neurones. HSV can reactivate from the latent state to produce infectious lesions. The HSV neurovirulence gene ICP34.5 is believed to condition post-mitotic cells (particularly neurones) for viral replication. (Thompson et al. Virology 172, 435-450 (1989); MacLean et al., J. Gen Virol. 72, 631-639 (1991); Harland and Brown, J. Gen Virol. 66, 1305-1321 (1985); and Taha et al., J. Gen Virol. 70, 705-716 (1989)). ICP34.5 deletion mutants cannot replicate in terminally differentiated cells but can lytically infect dividing cells (Brown, S. M et al. 75, 2367-2377 (1994)). The HSV-1 mutant strain 1716 is an ICP34.5 deletion mutant (EP-B-O 571,410) of HSV type I strain 17, that has reduced virulence and greatly reduced lethality in mice, but it replicates as efficiently as wild type virus in actively dividing tissue culture cells (Maclean, A. R. et al. J. Gen Virol. 72 631-639 (1991), Brown, S. M. et al, J. Gen Viral. 75 2367-2377 (1994)). The ability of ICP34.5 deletion mutants to specifically target and lyse dividing cells and not post mitotic cells makes them an attractive therapeutic agent for the treatment of cancer. HSV infection of rapidly dividing cancer cells leads to death of the cells by lysis. The 1716 mutant kills tumour cell lines in tissue culture and, in a range of in vivo cancer models, the virus was shown to induce tumour regression and prolong survival (Kesari, S., Randazzo, B. P. and Valyi-Nagy, T. Lab Invest. 73 636-648 (1995), MacKie E. A. et al. Br J. Cancer 74 745-752 (1996), Randazzo, B. P. et al. J. Invest Dermatol. 108 933-937 (1997)). In clinical trials, direct injection of 1716 was effective in treating patients with recurrent glioma (Rampling, R. et al. Gene Therapy 7 (10) 859-866 (2000)) and metastatic melanoma (MacKie, R. M., Stewart, B. and Brown, S. M. The Lancet 357 525-526 (2001)).

Significantly, in both of these trials there was no evidence for spread of 1716 to surrounding normal tissue. A second HSV-1 ICP34.5 deletion mutant, G207, which additionally lacks the UL39 gene that encodes the large subunit of the viral ribonucleotide reductase, has also been shown to be safe and effective in patients with malignant glioma (Markert, J. M. et al. Gene Therapy 7 (10), 867-874 (2000)).

Although strains such as 1716 and G207 that have impaired neurovirulence and that selectively infect dividing cells have strong therapeutic potential for the treatment of human malignancies, some limitations of their use are anticipated by the inventors. 1716 is able to infect and kill a variety of tumour cells in tissue culture, but its permissive range in vivo may be more restricted. For example, 1716 infection of B or T cell lymphomas has not been reported. Additionally, the virus may infect tumour cells less efficiently in vivo than in cell culture. The inventors have appreciated that it is desirable to overcome certain cell-type restrictions and increase the efficiency of infection of tumour cells so that modified HSV can be more widely, effectively and safely applied as an in vivo therapy.

Broadly, the present invention provides a means of altering or modifying the tropism of HSV, so that a particular range of cell types can be targeted.

At its most general, the present invention provides an HSV complex comprising a modified HSV and a targeting agent capable of targeting said modified HSV to a specific cell type, preferably a proliferating cell e.g. a cancer cell. The invention further provides a method of producing the HSV complex and its use of the complex in the treatment of diseases such as cancer.

Thus, in a first aspect, the present invention provides an HSV complex comprising an HSV linked to a targeting agent, capable of targeting a specific cell type, where the genome of said HSV is modified in the terminal portion of RL within Bam HI s (0-0.02 and 0.81-0.83 mu).

The targeting agent is conveniently an antibody or component of an antibody, e.g. an antibody binding domain. The antibody is preferably capable of specifically binding to a cell surface protein present of the cell type targeted. This is discussed below. The targeting agent is preferably linked to the modified virus via a viral envelope protein so that it is displayed on the surface of the virus. A convenient way of achieving this is to form a fusion protein comprising the targeting agent and a viral envelope protein such as a glycoprotein. Alternatively, the targeting agent may be linked to the viral particle by chemical means, e.g. co-valently, or by a binding agent, e.g. avidin/strepavidin and biotin.

In a preferred embodiment, nucleic acid encoding the targeting agent is incorporated into the viral genome so that it is expressed as a fusion protein with a viral envelope protein e.g. a glycoprotein, and as a result displayed on the surface of the particle.

Thus, the invention provides an HSV which is capable of targeting a specific cell type, said HSV lacking an expressible γ34.5 gene so as to lack neurovirulence and wherein the HSV expresses a targeting agent.

As an antibody binding domain forms a preferred embodiment of the invention, the following description will concentrate on the use of antibodies. However, it will be apparent to the skilled person that other targeting agents may be used, e.g. members of a specific binding pair such as a receptor and its ligand.

The antibody or antibody component incorporated into the viral envelope influences the selectivity of the virus by enhancing the efficiency of viral infection of a certain cell type or cell types. The HSV infection process is initiated through contact between glycoproteins of the viral envelope and glycoproteins of the target cell membrane. In the present invention, antibodies with specific affinity for membrane proteins of the chosen cell type are incorporated into the HSV viral envelope, increasing the affinity of the HSV for the surface of the chosen target cell through the additional interaction between the antibody and the cell surface protein. The binding of the antibody binding domain to its target antigen on the cell surface will bring both virion and cellular membranes into closer proximity and allow the viral envelope glycoproteins to initiate fusion of the membranes, leading to penetration of the cell.

The HSV-1 virion envelope contains at least 10 integral membrane glycoproteins, several of which mediate entry into mammalian cells. The initial interactions between the virus and the cell are between viral glycoproteins gB and/or gC and cell surface heparin sulphate proteoglycans, but this interaction is insufficient for viral penetration. Fusion of the viral and cellular membranes requires gD, gB and a gH/gL complex, and these proteins are presumed to act in concert. Specific receptor-mediated entry of HSV-1 involves interaction of gD with HVEM/HveA (herpesvirus entry mediator A), a lymphotoxin receptor and member of the TNF receptor family. Expression of HveA in CHO cells that are normally refractory to viral penetration rendered them permissive. Several other receptors have been identified using non-permissive CHO cells including the poliovirus receptor related proteins 1 and 2, now renamed HvecC and HvecB respectively. For this work, the inventors have been able to render a cell line normally resistant to infection permissive for HSV-1 entry.

The present invention uses an HSV that has an impaired ability to infect, replicate in or lyse terminally differentiated, non-dividing cells. In this form the virus is particularly suited for use as a therapeutic agent to treat diseases associated with proliferating cells such as cancer and non-cancer diseases such as Crohn's disease. The inventors believe the modified virus in accordance with the present invention will be particularly useful in targeting proliferating T-cells in cancer or non-cancer situations.

In a preferred embodiment, the HSV has been modified so that the gene encoding ICP 34.5 (gene γ34.5) is incapable of expressing a functional gene product.

The modified virus preferably contains a modification in respect of the wild type virus within the Bam HI s region of the internal repeat $R_L$ (0.81-0.83 mu) and within the counterpart region of the terminal $R_L$ (0-0.02 mu) such that the modified virus (variant) lacks neurovirulence.

The modification of the virus genome may be achieved by deletion of one or more nucleotides, insertion of additional nucleotides or any other alteration of the nucleotide sequence such as rearrangement, or substitution. Preferably, the modification of the HSV genome is achieved by deletion of one or more nucleotides.

The HSV may be a spontaneously isolated deletion variant of the wild type or it may be a wild type strain into which the desired modification has been introduced. Such modifications in the HSV may be made by genetic manipulation, for example by site-directed mutagenesis, or by excision of a portion of the genome with or without replacement with a pre-prepared DNA cassette incorporating the required modification.

Preferably, the HSV is HSV type I (HSV-I) even more preferably HSV-1 strain 17. In one embodiment, the HSV-1 strain will have a deletion of at least 100 nucleotides in the Bam HI s' region between Alu I site at 125074 nb and 125972 nb and within its counterpart sequence in $TR_L$.

More preferably 0.5 to 3 kb of the Bam HI s' region and its counterpart in $TR_L$ is deleted. Still more preferably about 0.7-2.5 kb is deleted.

Suitable modified HSV include HSV-1 mutant 1716 or G207. The production of HSV1716 is described in EP 571, 410-B which is incorporated herein by reference.

In addition to the above, the inventors have appreciated that, in order to treat a diverse range of tumours, the HSV complex in accordance with the invention will ideally have to be administered into the circulation of a patient. However, not only does the virus have to find the tumour cells (it can bind and be adsorbed by many different cell types) but it also has to contend with pre-existing immunological defenses (e.g. neutralising antibodies) designed to eliminate the virus. Pre-existing immunological defenses will be reasonably common as most people have had previous exposure to HSV-1. Given this, the present inventors have appreciated that there is a need to develop a "stealth" virus that avoids immunological detection and can specifically target tumour cells. Accordingly, the inventors have produced a stealth virus by eliminating the normal viral glycoproteins that mediate cell adsorption and replacing them with antibody-directed entry mediating glycoproteins incorporated into the virion structure. The principal viral glycoproteins involved in cell entry also provide the main neutralising epitopes and their removal will minimise immunological activity against such a virus. Thus, tumour antigen-directed HSV e.g. HSV1716 introduced into the circulation can target many tumour types including disseminated cancers that are either inaccessible or too numerous for direct injection or are too small to be detected.

Thus, the HSV complex as described above, e.g. HSV1716, that displays a tumour specific targeting antibody in accordance with the first aspect of the present invention, may be modified such that the genes encoding viral glycoproteins essential for normal cell entry (e.g. principally gD but also gC and/or gB, see below) are deleted or inactivated, thereby rendering the resulting virus dependent on tumour antigen/antibody interactions as the main route for cell infection. Deletion of these glycoproteins from the virus particle also removes the principal neutralising epitopes and therefore greatly reduces immunological defenses when administered systemically.

Therefore, the HSV complex according to the first aspect of the present invention may be further modified so that one or more viral glycoproteins, e.g. gD, gC and/or gB, are inactivated or deleted such that they are unable to mediate entry of the viral particle into cells. It is preferable that the one or more glycoproteins are modified at the genome level such that they cannot be expressed or cannot be expressed in a functional form. It is most preferable that the HSV genome is modified so that the one or more glycoproteins cannot be expressed at all as this will provide the HSV variant with the additional advantage that it can escape any pre-existing immunological defenses in vivo.

As mentioned above, the various glycoproteins may be modified or deleted from the viral particle, preferably at a nucleic acid level. The modification may include the incorporation of nucleic acid encoding the targeting agent so that the targeting agent is expressed on the surface of the particle. Thus, the HSV genome may be modified, in addition to the γ34.5 gene, such that one or more of the glycoproteins (e.g. gD, gC and/or gB) express the targeting agent, e.g. the antibody binding domain.

Preferably, the antibody or antibody component is specific for tumour surface antigen, i.e. antigen found on the surface of a tumour cell and associated with that cell, being either unique to tumour cells or being more abundant on tumour cells than on most if not all nontumour cells. Many novel or atypical forms of normal proteins are expressed by tumour cells, and antibodies directed against these provide tumour targeting strategies. For example, carcinoembryoinic antigen (CEA) is an important marker on many tumour cells and engineered antibodies directed against CEA have undergone clinical trials (Mayer, A. et al., J. Immunol. Methods 231 261-273 (1999)). Engineered antibodies directed against the Her2/neu growth factor (Trastuzamab) and against CD20 (rituximab) have been licensed for the treatment of breast cancer and Non-Hodgkin's lymphoma respectively Holliger, P. and Hoogenboom, H. (1998), Nature Biotechnology 16, 1015. CD55 (decay accelerating factor) is over-expressed by tumour cells to block complement activation and antibodies directed against CD55 may have therapeutic potential (Li, L. et al. B. J. Cancer 84 (1) 80-86 (2001)). Incorporation of an antibody binding domain that specifically targets tumour antigens such as CRA, Her2, CD20 and CD55 into the envelope of HSV will have the potential to alter its cellular tropism thus allowing infection of non-permissive tumour cells and possibly improving its ability to infect other tumour cells. For example, 1716 virions that display an antibody binding domain specific for CD20 may be able to infect and kill B-cell lymphomas.

Further, HSV, e.g. HSV1716 virions that display tumour targeting antibodies and from which the normal HSV-1 entry glycoproteins are deleted will only infect the targeted tumour cells.

The antibody binding domain may have specific affinity for a cell surface protein found on the cell type from which the tumour originated, e.g. in the case of a glioma, the antibody or antibody component incorporated into the HSV viral envelope would be specific for an antigen commonly associated with glial cells. The specificity of the avirulent HSV strain for infecting dividing cells would therefore be further modified so that glial cells were preferentially infected by the virus more than other types of dividing cells. By targeting dividing glial cells, the HSV should infect and lyse glioma cells more efficiently than any other cells. The use of antibodies or antibody components against particular cell types can also be used to extend the tropism of HSV to cell types that are not otherwise efficiently infected by HSV, e.g. the use of antibodies or antibody components specific for antigen found on B cells would be expected to extend the tropism of HSV to B cells. Antibodies or antibody components of different specificities may be included together in one HSV viral envelope. The combination of these specificities would be expected to give greater specificity of targeting to the desired cell type.

The antibody binding domain would preferably be fused to an integral membrane protein in the viral envelope, preferably an HSV glycoprotein. The preferred HSV-1 and HSV-2 glycoproteins are gB, gC and gD.

In a preferred embodiment, the antibody binding domain is in the form of a single chain variable fragment (scFv).

In a second aspect, the present invention comprises a method of making a modified HSV complex according to the first aspect of the invention comprising the step of infecting a cell line that constitutively expresses said fusion protein with an HSV, preferably a modified HSV, more preferably modified HSV-1.

In a third aspect, the present invention comprises a method of making a modified HSV complex according to the first aspect of the invention comprising the step of incorporating DNA encoding said fusion protein into the viral genome of the modified HSV.

In a fourth aspect, the present invention comprises the use of a modified HSV complex according to the first aspect of the invention in a method of medical treatment.

Preferably, the method comprises administering the HSV modified complex to a patient suffering from a disease associated with proliferation of cells, e.g. cancer, wherein the HSV complex selectively lyses dividing cells.

There is also provided a pharmaceutical composition which comprises the modified HSV in accordance with the present invention and a pharmaceutically acceptable carrier.

Pharmaceutical compositions comprising the modified HSV may be administered intravenously or directly injected into a tumour or infected site.

Aspects and embodiments of the present invention will now be illustrated, by way of example, with reference to the accompanying figures. Further aspects and embodiments will be apparent to those skilled in the art. All documents mentioned in this text are incorporated herein by reference.

FIG. 1. shows (a) the HSV-1 genome (with map units marked) in the prototype orientation; and (b) an expansion of BamHI k (s+g). The BamHI (B) and Alu (A) sites flanking the deletion in 1714/1716 are marked. All coordinates are based on the numbering of McGeoch et al. (1988). Also indicated are the positions of the 5' end of IE1, the "a" sequence, the $DR_1/U_b$ boudary in the "a" sequence, a 189 bp conserved open reading frame between HSV-1 and HSV-2 ($R_L$ ORF) and the end points of the 759 bp deletion in 1714/1716. The deletion extends from the $DR1/U_b$ boundary to remove the 5' 107 bp of the $R_L$ ORF.

Figure 2:
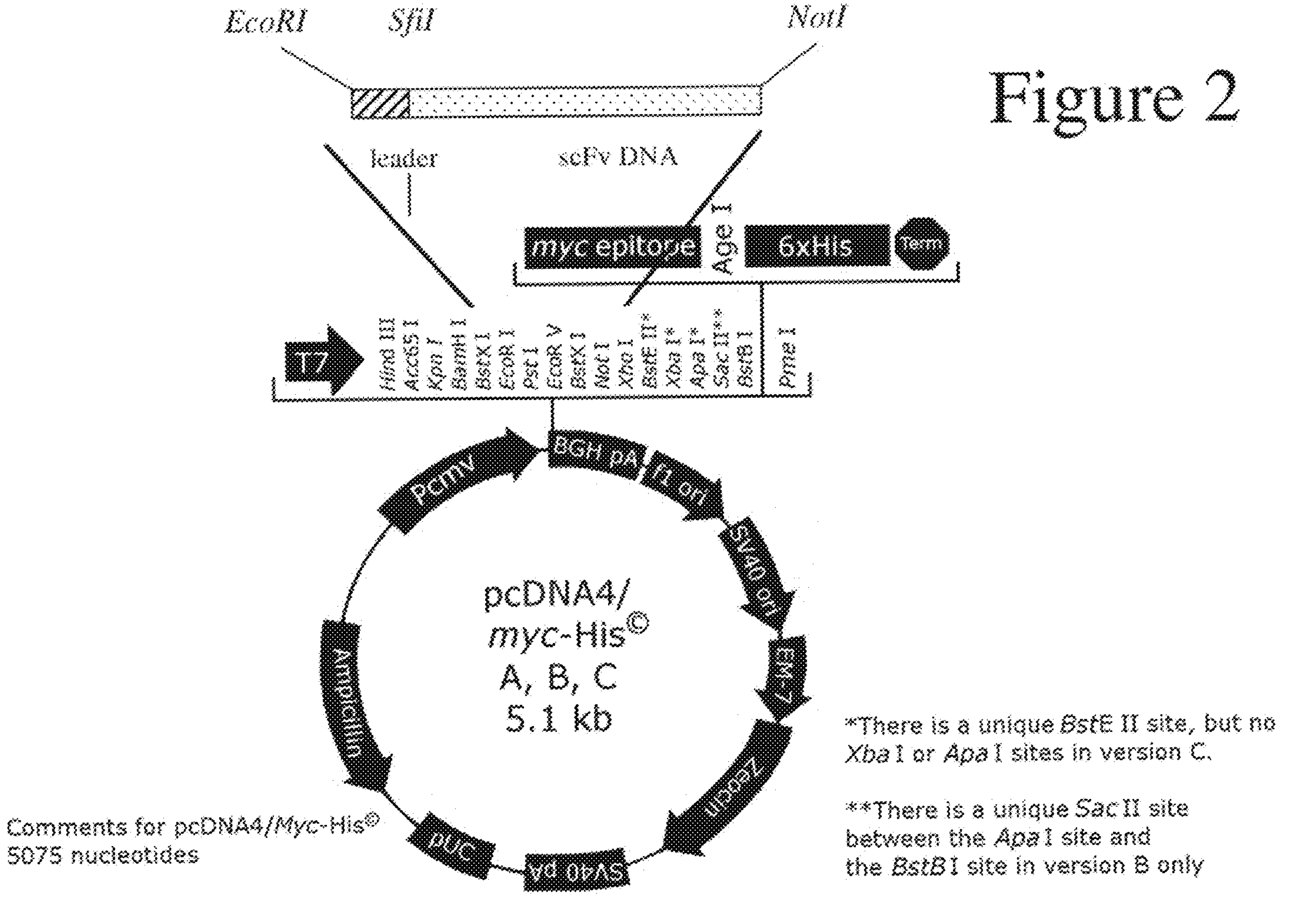

FIG. 2. Construction of the vector pEL4. a) Sequence of the 5' 99-mer oligonucleotide used to PCR amplify scFv DNA and simultaneously insert an IgG VH leader sequence (SEQ ID NO:1). The EcoRI site is underlined in red and the SfiI site is underlined in purple. The sequence between these two sites encodes the IgG VH leader sequence that will target the expressed protein to the secretory pathway of the cell. The sequence downstream of the SfiI site is from IgG VH. The 3' primer was from IgG VL and inserts a NotI site allowing PCR amplification of scFV DNA with 5' and 3' SfiI and NotI sites respectively. Following PCR the scFv DNA with IgG VH leader was cloned into the plasmid pcDNA4A to give pEL4.

Figure 3:
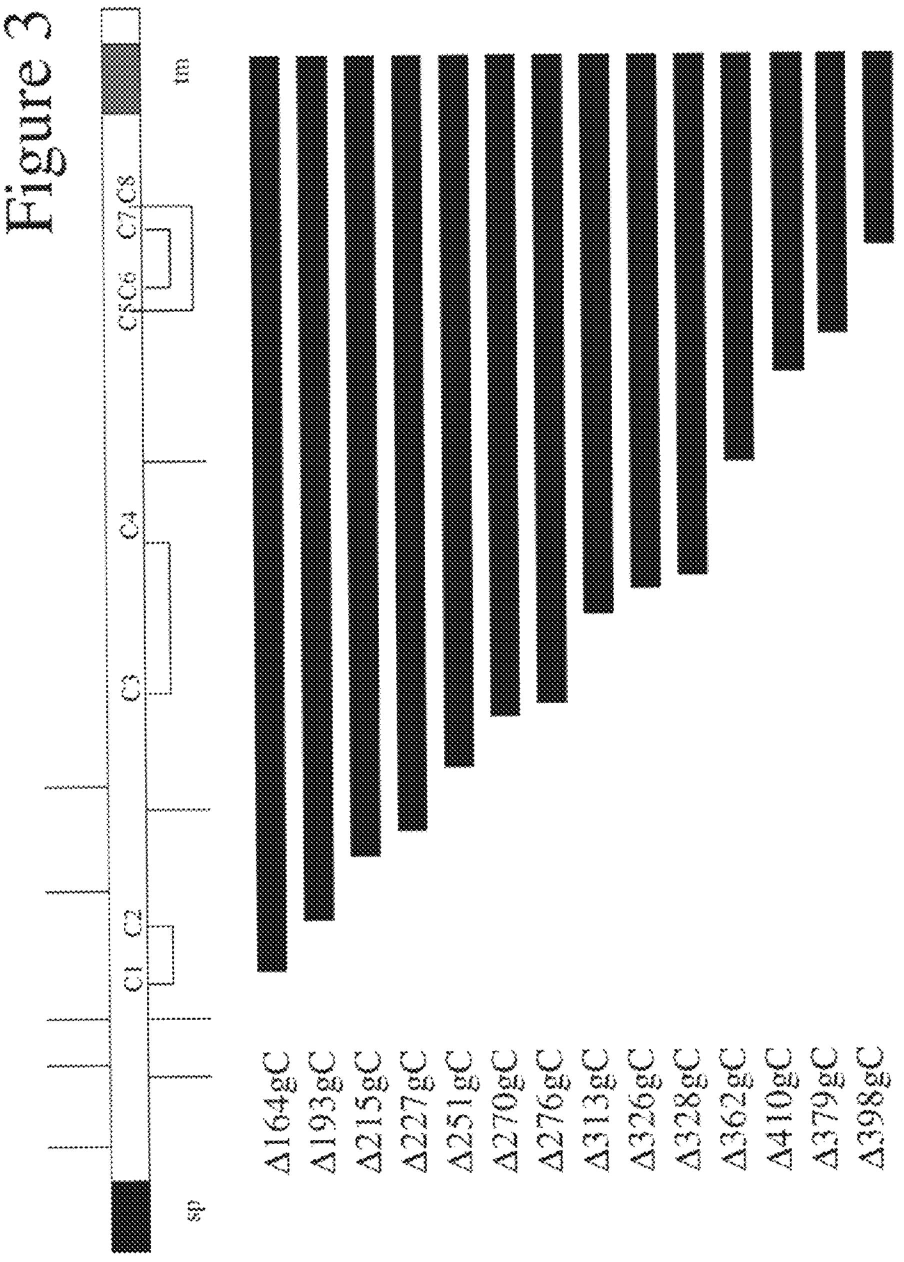

FIG. 3. Scale drawing of PCR-created N terminal deletions of HSV-1 gC. The full length gC protein is depicted at the top showing the signal peptide (sp) and transmembrane domain (tm). The 14 gC deletions shown below are designated according to the amino acid at their new N terminus. Thus Δ164gC has 163 amino acids deleted from its N terminus to give a gC fragment corresponding to amino acids 164-511.

Figure 4:
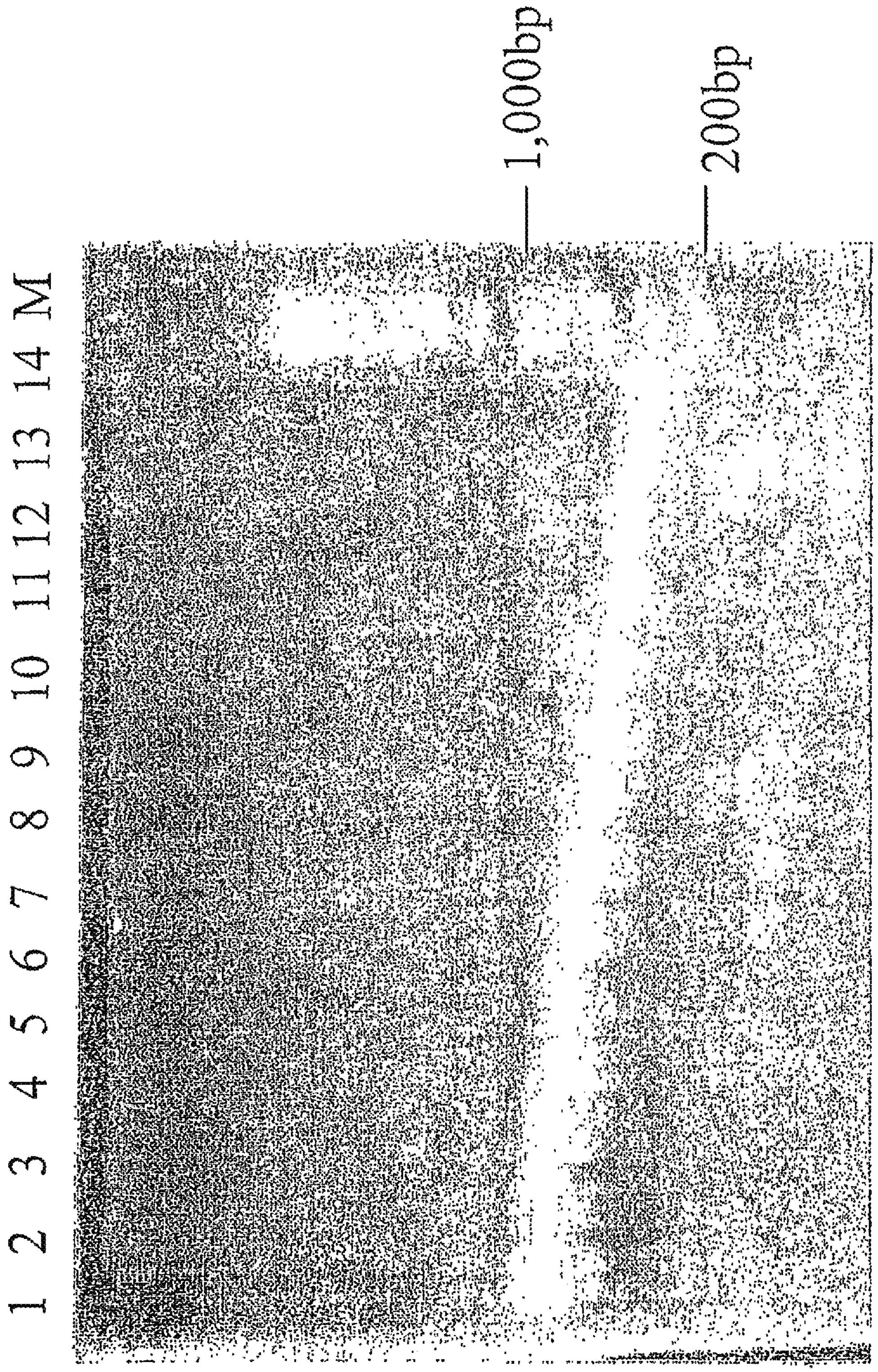

FIG. 4. 1% agarose gel that shows PCR amplification of sequentially deleted gC DNAs (lanes 114). M=DNA ladder with the location of the 200 bp and 1000 bp bands indicated. A common 3' PCR primer, corresponding to the C-terminus of gC but without the stop codons inserts an XbaI site and allows cloning in-frame with the vector myc and 6-his tags. The 5' primers used were randomly selected from the gC coding sequence to give sequential deletions of between 6-90 nucleotides. The 5' primer inserts a NotI restriction site that allows the gC DNA to be cloned in-frame with the scFv DNA in pEL4. NotI/XbaI digested PCR amplified DNAs were cloned into pEL4 digested also with these enzymes to give scFv/gC fusion protein expression constructs.

Figure 5:
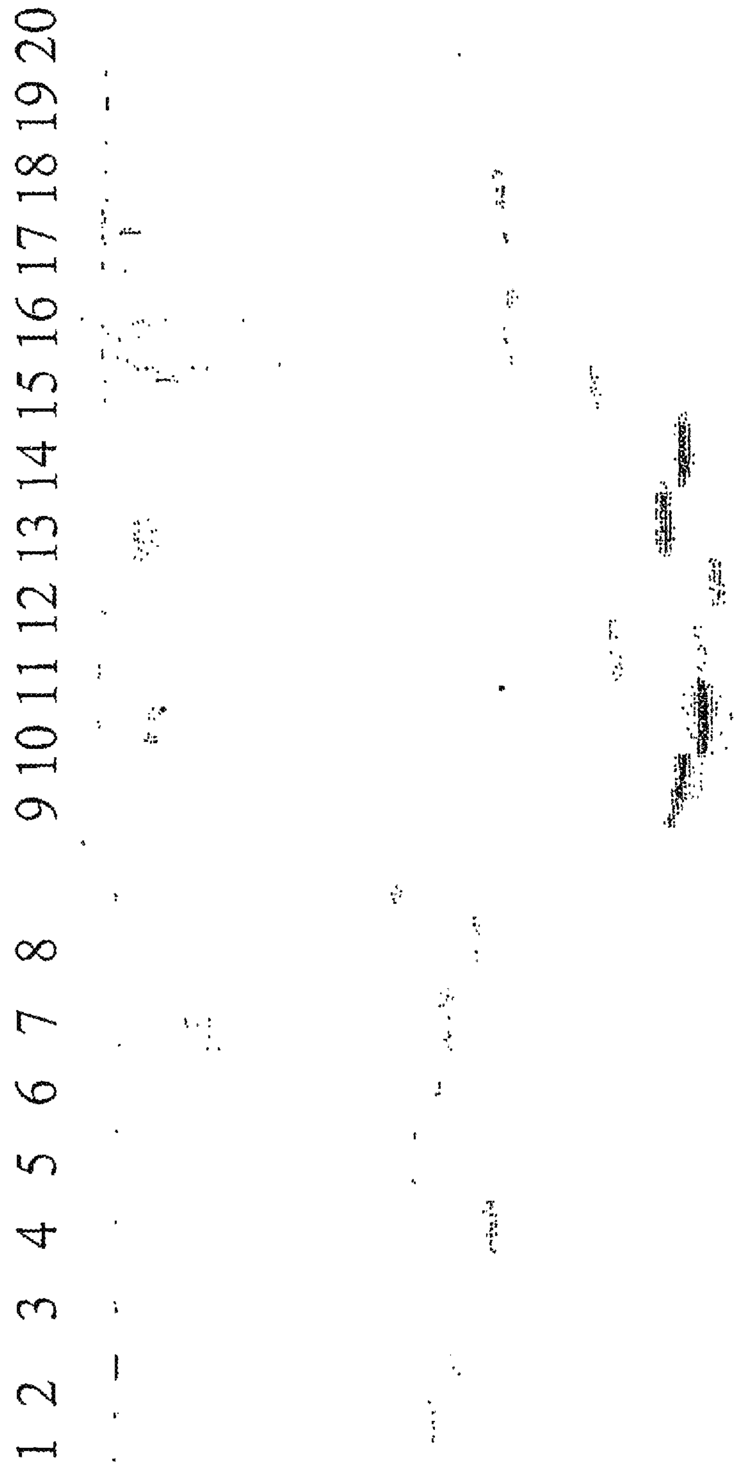

FIG. 5. Western blots that show expression of scFv/gC fusion proteins in whole cell extracts and their incorporation into HSV1716 virus particles. Lanes 5-8, 9-11, 16 and 17 are whole cell extracts. Lanes 1-4, 12-15 and 18 are virus preparations. Lanes 1 and 5=Δ193gC, lanes 2 and 6=Δ215gC, lanes 3 and 7=Δ251gC, lanes 4 and 8=Δ328gC, lanes 9 and 13=Δ410gC, lanes 10 and 14=Δ424gC, lanes 11 and 15=Δ362gC, lane 12=Δ457gC, lanes 16-18=Δ227gC. Lanes 19 and 20 show mock virus preparations made from cell lines expressing Δ227gC and Δ424gC respectively, no bands were detected in these samples. Note that the cell line expressing Δ251gC gives a strong band in the cell extract (lane 7) but shows only a weak band in the virus preparation (lane 3). In contrast to this, Δ328gC is expressed at intermediate levels in the cell line but gives a strong band with its virus preparation. The overall results are summarized in Table 1.

EXAMPLE 1

Method of Making HSV-1 1716 Strains Wherein Fusion Proteins Between Anti-Tumour ScFvs and Envelope Glycoproteins B, C and D are Incorporated into the Virion Envelope Recombinant scFv variants of monoclonal antibodies that bind different extracellular epitopes of CD55 are derived by standard protocols (see Pope, A. R., Embleton, M. J. and Mernaugh, R. (1996) In Antibody Engineering (eds McCafferty, Hoogenboom and Chiswell) Practical Approach Series, Oxford University Press Inc., New York. 1-40). scFv are particularly suitable for incorporation into the fusion protein because they are encoded by a single nucleotide sequence. scFv can be conveniently engineered using recombinant antibody technology (Hoogenboom, H. R. and Chames, P. Immunology Today 21 (8) 371-377 (2000)). Recombinant antibodies are predominantly produced using mRNA isolated from hybridomas or from populations of lymphocytes isolated either from the spleens of immunized animals or from human binding sites are amplified separately by RT-PCR and fused to produce fragments encoding single chain antibody molecules (the scFv). The scFv polypeptide effectively recreates the antigen recognition site in a single protein that retains high affinity binding. The cloned scFv can readily be genetically fused with the domains of other proteins, for example, with the M13 gIII coat protein for display on phages or to the enzyme carboxypeptidase G2 for antigen directed enzyme prodrug therapy (ADEPT).

Following RT-PCR cloning, sequencing and linkage of the antibody VH and VL for each monoclonal antibody, the scFv-encoding DNAs will be amplified using PCR primers that incorporate SfiI and NotI restriction enzymes sites at the 5' and 3' ends respectively for cloning in the phagemid vector pHEN2 or for construction of fusion proteins. The choice of restriction enzyme sites will depend on the sequences of the scFv and glycoproteins used *E. coli* HB2151 will be transformed with the phagemid vectors and scFvs expressed by IPTG induction. ScFv expressed from pHEN2 have c-myc and 6-his tags for purification/detection. The reactivities of the recombinant scFv will be compared with their respective monoclonal counterparts by Western Blotting and FACS analysis using CHO cells stably transfected with plasmid that expresses their target antigens.

DNA encoding an scFv with an IgG VH leader sequence was cloned into the plasmid pcDNA4 (Invitrogen) to create the vector pEL4 (FIG. 2). The 5' primer used to amplify the scFv DNA incorporates an IgG VH leader sequence, linked to the scFv DNA by a SfiI site. The primer also inserts an EcoRI site 5' to the IgG VH leader sequence. The scFv DNA can be removed and replaced by alternative scFv DNAs using SfiI/NotI digestion. The leader sequence can be removed by EcoRI/SfiI digestion and replaced with other leader sequences, e.g., gC signal peptide sequences. Such leader sequences with EcoRI/SfiI restriction sites can be obtained either by PCR using appropriate primers or by using chemically synthesised complementary oligonucleotides.

A number of HSV-1 strain $17^+$ gB, gC and gD DNA fragments are PCR-cloned from the viral genome using methods which have previously been successful for other herpesvirus proteins (Sun, Y. and Conner, J. (1999) The U28 ORF of human herpesvirus-7 does not encode a functional ribonucleotide reductase R1 subunit. Journal of General Virology 80: 2713-2718. Sun, Y. and Conner, J. (2000) Characterisation of hetero-subunit complexes formed by herpes simplex type 1 and equine herpes virus type 4 ribonucleotide reductase R1 and R2 subunits. Biochem J. 347, No 1: 97-104. Incorporated herein by reference. The primers used to amplify the DNAs will incorporate appropriate restriction enzyme sites for fusion to the scFv DNA and cloning into pEL4. PCR primers for amplification of glycoprotein DNA will be designed such that a series of random, sequentially deleted N-terminally truncated proteins are expressed, each deletion will remove approximately 2-30 amino acids up to the region encoding the transmembrane domain. For example, gC comprises 511 amino acids with the transmembrane region located downstream of amino acid 479, a family of 14 sequentially deleted N-terminally truncated polypeptides (FIG. 3) for fusion to scFvs have been cloned. Examples of PCR-amplified gC DNAs are shown in FIG. 4. The primers used for PCR amplification of the gC DNA fragments incorporated NotI and XbaI sites at the 5' and 3' ends respectively. PCR-amplified DNA was digested directly with the appropriate enzymes (i.e. NotI/XbaI for gC fragments) and cloned into pEL4 digested also with these enzymes. The resulting constructs express scFv/gC fusion proteins with C-terminal myc and 6-his tags, under control of the CMV IE promoter. The promoter and tags are provided by the pcDNA4 backbone of pEL4 as is a zeocin resistance gene that allows production of stable cell lines using antibiotic selection. DNA fragments were also cloned into the PCR-cloning vector pGEM-T Easy and sequenced to ensure that no PCR-induced mutations have been incorporated.

BHK cells were transiently transfected with each of the pEL4 constructs using lipofectamine and, after 48 hrs, zeocin selection (10 ug/ml) was initiated. Cells were selected with zeocin for approximately 21 days and extracts prepared for western blotting. For each cell line, a polypeptide of the appropriate molecular size for the scFv/gC fusion protein was detected with the anti-myc tag monoclonal antibody 9B11 (New England Biolabs).

Examples of expression are shown in FIG. 5 and estimates for the levels of expression in each of the cell lines using the Western blot data are presented in Table 1. Immunofluorescence using 9B11 and an anti-murine IgG/FITC conjugate demonstrated a perinuclear/Golgi localisation for all of the expressed fusion proteins. Incorporation of scFv/glycoprotein fusion proteins into the HSV1716 envelope using stably transfected BHK expressing cell lines was analysed by Western blotting with 9B11. HSV1716 at 10 pfu/cell was used to infect each of the cell lines and virus harvested from the culture medium 24-28 hours later was analysed by Western blotting with 9B11. Examples are shown in FIG. 5 and results summarised in Table 1. No myc-tagged proteins were detected in similar preparations made from mock-infected cells. Most scFv/gC fusion proteins were incorporated into the virus (Table 1). Some were more efficiently incorporated than others (e.g., Δ328gC and Δ457gC are expressed at intermediate levels in their respective cell lines but are present as strong bands in their virus preparations) whereas incorporation of others expressed at high levels in their cell line was poor (e.g., Δ251gC).

Recombinant viruses expressing the most appropriate scFv/glycoprotein fusions are created using a variant of 1716 that expresses green fluorescent protein (GFP). Incorporation of scFv/glycoprotein fusions are confirmed as described above.

EXAMPLE 2

Infection of BHK Cells by HSV-1 Incorporating ScFv-Glycoprotein Fusion Proteins The ability of the viruses incorporating ScFv-glycoprotein fusion (as produced in example 1) to infect BHK cells is analysed by single-step growth experiments and compared with 1716. The tropism of these scFv-glycoprotein fusion viruses is investigated using CHO cells that constitutively express CD55. Penetration of the viruses into CHO cells is confirmed using GFP reporter gene analysis.

Results in CHO cells will identify the factors that allow antibody-mediated viral infection and recombinant viruses will be created by cloning the appropriate scFv/glycoprotein DNA into the viral genome. The genomes of these viruses can be further modified by deletion or inactivation of glycoprotein genes such as gD, gC and gB using for example, homologous recombination.

By accumulating monoclonal antibodies to tumour specific antigens such as CEA or CD20, it is then possible to construct a panel of oncolytic herpesviruses with improved targeting to the tumour of choice.

TABLE 1

Expression in cells and incorporation into HSV1716 of scFv/gC fusion proteins. Expression in cells and incorporation into virus were determined by Western blotting.

| fusion protein | Expression in cells | Incorporation into virus |
|---|---|---|
| Δ164gC | ++ | − |
| Δ193gC | ++ | ++ |
| Δ215gC | ++ | ++ |

TABLE 1-continued

Expression in cells and incorporation into HSV1716 of scFv/gC fusion proteins. Expression in cells and incorporation into virus were determined by Western blotting.

| fusion protein | Expression in cells | Incorporation into virus |
|---|---|---|
| Δ227gC | +++ | ++ |
| Δ251gC | +++ | + |
| Δ270gC | − | − |
| Δ276gC | +++ | +++ |
| Δ313gC | + | + |
| Δ326gC | − | − |
| Δ328gC | ++ | +++ |
| Δ362gC | ++ | ++ |
| Δ410gC | +++ | +++ |
| Δ424gC | +++ | +++ |
| Δ457gC | ++ | +++ |

+++ = strong reactivity, ++ = intermediate, + = weak and − = undetected

The invention claimed is:

1. A method of producing an HSV which is capable of targeting a tumor cell which expresses a tumor surface antigen comprising:
   (a) modifying the HSV genome by incorporating nucleic acid encoding an antibody binding domain which is expressed as a fusion protein with HSV glycoprotein gC or gD, wherein said antibody binding domain is capable of specifically binding to the tumor surface antigen on the tumor cell; and
   (b) expressing the modified HSV in a cell.

2. A method according to claim 1 which further comprises modifying the HSV genome so as to prevent γ34.5 gene from expressing a functional protein.

3. A method according to claim 1 wherein said antibody binding domain is in the form of a Single Chain Variable fragment (ScFv).

4. A method according to claim 1 wherein said antibody binding domain is an antibody.

5. A method according to claim 1 wherein the tumour surface antigen is CEA, Her2, CD20 or CD55.

6. A method according to claim 1 wherein the HSV is a γ34.5 deletion mutant.

7. A method according to claim 1 wherein the HSV is HSV-1.

8. A method according to claim 1 wherein the HSV is HSV-1 strain 17.

9. A method according to claim 1 wherein the HSV is HSV1716.

10. A method according to claim 1 further comprising additionally modifying one or more viral glycoproteins.

11. A method according to claim 10 wherein the additional one or more viral glycoproteins are deleted.

12. A method according to claim 10 wherein the additional one or more viral glycoproteins are modified by incorporation of the targeting agent.

13. A method according to claim 10 wherein the additional one or more viral glycoproteins are gD, gC and/or gB.

* * * * *

SEQUENCE LISTING

<160> NUMBER OF SEQ ID NOS: 1

<210> SEQ ID NO 1

<211> LENGTH: 99

<212> TYPE: DNA

<213> ORGANISM: Artificial sequence

<220> FEATURE:

<223> OTHER INFORMATION: synthetic

<400> SEQUENCE: 1

```
gaattcatgg gatggagctg tatcatcctc ttcttggtag caacagctac aggtgtccac      60

tccgcggccc agccggccga tgtgcaactg gtggagtct                              99
```